United States Patent
Gidekel et al.

(10) Patent No.: US 11,534,449 B2
(45) Date of Patent: Dec. 27, 2022

(54) TRICIN DERIVATIVES AND COMPOSITIONS THEREOF FOR CANCER TREATMENT

(71) Applicant: NEOCAGE SL, Canillo (AD)

(72) Inventors: Manuel Gidekel, Canillo (AD); Jose Luis Novella Robisco, Madrid (ES); Mario Nicolas Banduc, Santiago (CL)

(73) Assignee: NEOCAGE SL, Canillo (AD)

( * ) Notice: Subject to any disclaimer, the term of this patent is extended or adjusted under 35 U.S.C. 154(b) by 855 days.

(21) Appl. No.: 16/275,531

(22) Filed: Feb. 14, 2019

(65) Prior Publication Data

US 2020/0261486 A1   Aug. 20, 2020

(51) Int. Cl.
*A61K 31/7048* (2006.01)
*A61P 35/00* (2006.01)
*A61K 35/30* (2015.01)

(52) U.S. Cl.
CPC .......... *A61K 31/7048* (2013.01); *A61K 35/30* (2013.01); *A61P 35/00* (2018.01)

(58) Field of Classification Search
CPC ................................................ A61K 31/7048
See application file for complete search history.

(56) References Cited

U.S. PATENT DOCUMENTS

2017/0049839 A1* 2/2017 Gidekel ................. A61P 35/00

OTHER PUBLICATIONS

Malvicini, M. et al., Molecular Cancer Therapeutics, 2018, vol. 17, No. 5, pp. 966-976 (Year: 2018).*
Redondo-Blanco, S. et al., Frontiers in Pharmacology, "New Insights toward Colorectal Cancer Chemotherapy Using Natural Bioactive Compounds", 2017, vol. 8, No. 109, pp. 1-22 (Year: 2017).*
Tung, Y.-C. et al., Current Pharmacology Reports, Polymethoxyflavones: Chemistry and Molecular Mechanisms for Cancer Prevention and Treatment, Feb. 7, 2019, vol. 5, pp. 98-113 (Year: 2019).*
Zips, D. et al., In Vivo, "New Anticancer Agents: In Vitro and In Vivo Evaluation", 2005, vol. 19, pp. 1-8 (Year: 2005).*

* cited by examiner

*Primary Examiner* — Bahar Craigo
(74) *Attorney, Agent, or Firm* — Meunier Carlin & Curfman LLC

(57) ABSTRACT

Provided are compositions and methods for treatment of cancer and for adoptive T cell therapy (ACT). The compositions comprise one or more derivatives of tricin 7-O-β-D-glucopyranoside (ANTARTINA®). The compositions comprise one or more pharmaceutically acceptable excipients convenient for delivery of the tricin 7-O-β-D-glucopyranoside derivatives. Tricin 7-O-β-D-glucopyranoside derivatives described herein include acetylated tricin 7-O-β-D-glucopyranoside, as well as glucose, maltose, cellobiose, lactose, xylose, and galactose derivatives. The methods include treatment, or reduction in the risk of suffering from, colorectal cancer and hepatocellular cancer.

10 Claims, 11 Drawing Sheets

TRICIN DERIVATIVES AND COMPOSITIONS THEREOF FOR CANCER TREATMENT

CROSS-REFERENCE TO RELATED APPLICATIONS

This application claims priority to U.S. Provisional Patent Application Ser. No. 62/710,271 filed in the United States on Feb. 27, 2018, the entire contents of which is hereby incorporated by reference for all purposes.

FIELD OF THE INVENTION

The molecules disclosed herein are tricin derivatives useful for treatment of cancers, such as colorectal carcinoma (CRC) and others. The molecules are derivatives of ANTARTINA® (tricin 7-O-β-D-glucopyranoside). The molecules provide an immune response against CRC as shown by CTL assay, analyzing dendritic cell activation and antratumor T cell sub-populations, and tumor re-challenge experiments. This tricin derivative is also shown to induce a potent specific cytotoxic T cell response against CRC and long lasting antitumor activity. These tricin derivatives are therefore useful in methods of treating and/or prevent occurrence of CRC and other cancers in mammals.

BACKGROUND

Colorectal carcinoma (CRC) is a major cause of cancer-related morbidity and mortality worldwide and is responsible for nearly 700,000 deaths each year. (Torre et al., "Global cancer statistics," *CA Cancer J. Clin.*, 65(2):87-108, 2015). For metastatic disease, surgery is a potential curative option, but less than 20-30% of patients are suitable for resection due to clinical or technical issues, including extra-hepatic disease. (Zampino et al., *Crit. Rev. Oneal. Hematol.*, 2016, 108:154-63). In the last few years, multidisciplinary approaches, such as chemotherapy regimens, radio embolization, and targeted therapies, have been applied to improve patient survival, but as noted above there still remains a significant mortality rate. (Elias et al., *Liver Cancer*, 2016, 6(1):90-8). Therefore, new therapeutic therapies are needed for patients with a more advanced stage of the disease (Prieto et al., *Surg. Clin. North Am.*, 2004, 84(2):673-96).

With its unique weather and environmental characteristics, *Antarctica* is home to an extraordinary variety of extremophile organisms including vascular plants such as *Deschampsia Antarctica*. (Alberti et al., *Physiol. Plant.*, 2002, 115(4):479-86). There are several examples of novel psychrophilic enzymes and new molecules isolated from organisms found in *Antarctica* with potential uses in medicine. (Cavicchioli et al., *Curr. Opin. Biotechnol.*, 2002, 13(3):253-61). In particular, *Deschampsia antarctica* is able to tolerate high UV exposure due to the production of secondary metabolites as photoprotector agents, especially flavonoid-like molecules. (Bravo et al., *J. Exp. Bot.*, 2005, 56(414):1189-96, and van de Staaij et al., *J. Photochem. Photobiol. B*, 2002, 66(1):21-9).

The reported antitumor activities of flavonoids involve the inhibition of proliferation and induction of apoptosis, suppression of protein tyrosine kinase activity, and anti-angiogenic effects. (Middleton et al., *Pharmacol. Rev.*, 2000, 52(4):673-751). However, little is known about the role of tricin derivatives and their bioactivity as anticancer molecules. ANTARTINA® (tricin 7-0-beta-D glucopyranoside) was isolated from the Antarctic plant *Deschampsia antarctica* and has been previously reported from other plants. (Hidalgo et al., *Mol. Cancer Ther.*, 2011, 10(8):1311-6, and Rubio-Viqueira et al., *Clin. Cancer Res.*, 2006, 12(15):4652-61).

Due to low natural availability, a synthesis was conducted. Various observations have been reported on the antitumor activity of ANTARTINA® produced synthetically. (See, U.S. Pat. No. 10,058,582, PCT Publication No. WO 2009/064480, and Malvicini et al., *Mol. Cancer Therap.*, 2018, 17(5):966-976).

Here, it is shown that ANTARTINA® derivatives, such as acetylated ANTARTINA®, in combination with immune-gene therapy using an adenovirus encoding IL-12, induces a potent antitumoral response against CRC in mice when combined with AdIL-12 It is also disclosed that acetylated ANTARTINA® has a superior antitumoral effect in comparison with native ANTARTINA® in mice with CRC. Thus, disclosed herein, it is revealed that ANTARTINA® in combination with immuno-gene therapy (adenovirus-IL12) shows a synergistic antitumoral effect 80% remission. Additionally, analogues or derivatives of ANTARTINA® are shown to have a potent effect on hepatocarcinoma cells.

SUMMARY

Disclosed are methods and compositions for treating cancer in a subject in need thereof. The methods described herein comprise administering a pharmaceutically effective composition comprising one or more derivatives of tricin 7-O-β-D-glucopyranoside (ANTARTINA®). The one or more derivatives of tricin 7-O-β-D-glucopyranoside are shown in FIG. 1. The derivatives are one or more of: acylated tricin 7-O-β-D-glucopyranoside (6a), [3,4,5-triacetoxy-6-[5-hydroxy-2-(4-hydroxy-3,5-dimethoxy-phenyl)-4-oxo-chromen-7-yl]oxy-tetrahydropyran-2-yl]methyl acetate (5b), 5-hydroxy-2-(4-hydroxy-3,5-dimethoxy-phenyl)-7-[3,4,5-trihydroxy-6 (hydroxymethyl)tetrahydropyran-2-yl]oxy-chromen-4-one (1b), xylose tricin 7-O-β-D-glucopyranoside (1c), 7-[(3R,4R,5S,6R)-3,4-dihydroxy-6-(hydroxymethyl)-5-[(3R,4S,5R,6R)-3,4,5-trihydroxy-6-(hydroxymethyl)tetrahydropyran-2-yl]oxy-tetrahydropyran-2-yl]oxy-5-hydroxy-2-(4-hydroxy-3,5-dimethoxy-phenyl) chromen-4-one (1d), 7-[(3R,4R,5S,6R)-3,4-dihydroxy-6-(hydroxymethyl)-5-[(3R,4S,5S,6R)-3,4,5-trihydroxy-6-(hydroxymethyl)tetrahydropyran-2-yl]oxy-tetrahydropyran-2-yl]oxy-5-hydroxy-2-(4-hydroxy-3,5-dimethoxy-phenyl) chromen-4-one (1e), and 7-[(2S,3R,4R,5S,6R)-3,4-dihydroxy-6-(hydroxymethyl)-5-[(2S,3R,4S,5S,6R)-3,4,5-trihydroxy-6-(hydroxymethyl)tetrahydropyran-2-yl]oxy-tetrahydropyran-2-yl]oxy-5-hydroxy-2-(4-hydroxy-3,5-dimethoxy-phenyl)chromen-4-one. In certain embodiments of the described methods, the cancer is colorectal cancer or hepatocellular carcinoma. In such methods, the subject is any mammal, but is in some embodiments a human.

In certain embodiments of the described methods, the colorectal cancer is an adenocarcinoma, a gastrointestinal carcinoid tumor, a colorectal lymphoma, a gastrointestinal stromal tumor, a leiomyosarcoma, or a melanoma.

In a particular embodiment of the disclosed methods of treating cancer, the one or more derivatives of tricin 7-O-β-D-glucopyranoside is acylated tricin 7-O-β-D-glucopyranoside.

In the presently disclosed methods, the treating of cancer comprises any or all of reducing the proliferation of cancer cells in the subject, reducing the size of one or more tumors in the subject, reducing the risk of mortality of the subject from cancer, or extending the life of the subject.

In some embodiments of the described methods, the method further comprises administering to the subject one or more additional antitumor agents in a combination anticancer therapy. In certain such embodiments, the one or more additional antitumor agents is one or more checkpoint inhibitors. The one or more antitumor agents are, for example, one or more monoclonal antibodies.

Also described herein are several derivatives of tricin 7-O-β-D-glucopyranoside, including acylated tricin 7-O-β-D-glucopyranoside (6a), [3,4,5-triacetoxy-6-[5-hydroxy-2-(4-hydroxy-3,5-dimethoxy-phenyl)-4-oxo-chromen-7-yl]oxy-tetrahydropyran-2-yl]methyl acetate (5b), 5-hydroxy-2-(4-hydroxy-3,5-dimethoxy-phenyl)-7-[3,4,5-trihydroxy-6(hydroxymethyl)tetrahydropyran-2-yl]oxy-chromen-4-one (1b), xylose tricin 7-O-β-D-glucopyranoside (1c), 7-[(3R,4R,5S,6R)-3,4-dihydroxy-6-(hydroxymethyl)-5-[(3R,4S,5R,6R)-3,4,5-trihydroxy-6-(hydroxymethyl)tetrahydropyran-2-yl]oxy-tetrahydropyran-2-yl]oxy-5-hydroxy-2-(4-hydroxy-3,5-dimethoxy-phenyl)chromen-4-one (1d), 7-[(3R,4R,5S,6R)-3,4-dihydroxy-6-(hydroxymethyl)-5-[(3R,4S,5S,6R)-3,4,5-trihydroxy-6-(hydroxymethyl)tetrahydropyran-2-yl]oxy-tetrahydropyran-2-yl]oxy-5-hydroxy-2-(4-hydroxy-3,5-dimethoxy-phenyl)chromen-4-one (1e), and 7-[(2S,3R,4R,5S,6R)-3,4-dihydroxy-6-(hydroxymethyl)-5-[(2S,3R,4S,5S,6R)-3,4,5-trihydroxy-6-(hydroxymethyl)tetrahydropyran-2-yl]oxy-tetrahydropyran-2-yl]oxy-5-hydroxy-2-(4-hydroxy-3,5-dimethoxy-phenyl)chromen-4-one (see FIG. 1).

Thus, disclosed herein are compositions comprising the derivatives of tricin 7-O-β-D-glucopyranoside. Such compositions comprise one or more of these derivative compounds. In certain embodiments, the compositions further comprise one or more pharmaceutically acceptable excipients, as are known in the art to be useful for administering such compositions to a subject in need thereof.

Also disclosed are methods of adoptive T cell therapy (ACT). Such methods comprise various steps including removing dendritic cells from the subject, isolating the dendritic cells, exposing the dendritic cells to the compositions described herein comprising one or more derivatives of tricin 7-O-β-D-glucopyranoside to activate the dendritic cells, and injecting the activated dendritic cells into the subject, thereby generating an immunoprotective response in the subject. In some embodiments the subject from which the dendritic cells were obtained is the same subject into which the activated dendritic cells are injected.

In such ACT methods, the subject in need thereof, in some embodiments, has or has been diagnosed with, or is at risk of cancer. In certain embodiments of such ACT methods the cancer is colorectal cancer or hepatocellular carcinoma. In certain embodiments of the described ACT methods, the composition to which the dendritic cells are exposed ex vivo comprises or consists of or consists essentially of tricin 7-O-β-D-glucopyranoside, and/or acylated tricin 7-O-β-D-glucopyranoside (6a).

Thus, provided herein are methods of reducing the proliferation of cancer cells, reducing the size of one or more tumors, reducing a risk of mortality due to cancer, or extending a life of a subject in need thereof, which comprises administering to the subject in need thereof a pharmaceutically effective amount of acylated tricin 7-O-β-D-glucopyranoside (6a), wherein the subject is at risk of colorectal cancer or has been diagnosed with colorectal cancer.

DETAILED DESCRIPTION

Figure 1:
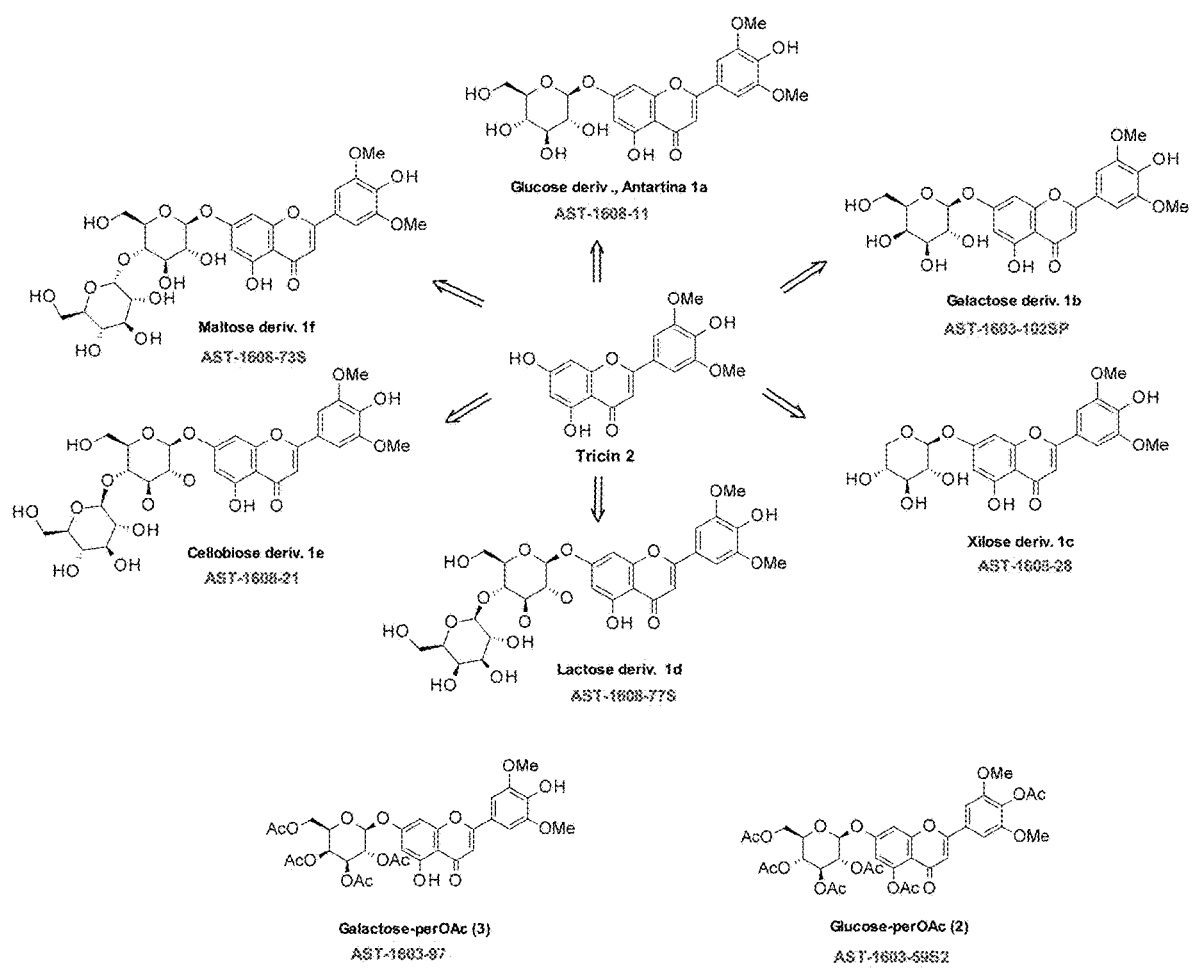
FIG. 1 depicts the chemical structure of tricin and ANTARTINA® and related derivatives and analogues synthesized and tested as described herein ("Antartina 1a" corresponds to ANTARTINA®).

In colorectal carcinoma (CRC) patients, distant metastatic disease is present at initial diagnosis in nearly 25% of patients. The majority of patients with metastatic CRC have an incurable disease; therefore, new therapies are needed to address this cancer. Agents derived from medicinal plants have already demonstrated therapeutic activities in human cancer cells. ANTARTINA® is an antitumor agent isolated from *Deschampsia antarctica* Desv. In that study, the aim was to evaluate the antitumor properties of ANTARTINA® in CRC models. Human and murine CRC cell lines were employed to investigate proliferation, apoptosis, and cell cycle effects of ANTARTINA® therapy in vitro. Immune response of ANTARTINA® against cancer cells in the CRC model was also investigated using a cytotoxic T lymphocyte (CTL) assay, analyzing dendritic cell activation and intratumor T cell sub-population, and by tumor re-challenge experiments.

ANTARTINA® inhibits in vitro human CRC cell proliferation. In an immunocompetent CRC mouse model, ANTARTINA® potently inhibited tumor growth and liver metastases, leading to complete tumor regressions in >30% of mice, along with an increased animal survival rate. In addition, ANTARTINA® induced a potent specific cytotoxic T cell response against CRC and a long lasting antitumor immunity. Interestingly. ANTARTINA® increased tumor immunogenicity and stimulated dendritic cell activation. No toxic effects were observed at the doses employed. These findings show that ANTARTINA® has the ability to induce antitumor immunity against CRC and is useful for the treatment of CRC.

While various aspects and embodiments have been illustrated and described in detail, above, such illustration and description are to be considered illustrative or exemplary and not restrictive. It will be understood that changes and modifications can be made by those of ordinary skill within the scope and spirit of the following claims. In particular, this description is intended to encompass further embodiments with any combination of features from different embodiments described above and below.

The compositions and methods described herein are additionally described by way of the following illustrative non-limiting examples that provide a better understanding of these embodiments and their many advantages. The following examples are included to demonstrate certain useful embodiments. It should be appreciated by those of skill in the art that the techniques disclosed in the examples which follow represent compositions and methods that function well, and thus can be considered to constitute preferred embodiments. However, those of skill in the art should, in light of the present disclosure, appreciate that many changes can be made in the specific embodiments that are disclosed and still obtain a like or similar result without departing from the spirit and scope of this disclosure.

EXAMPLES

Melting points were determined in open capillary tubes with a Stuart Scientific SMP3 melting point apparatus. Infrared (IR) spectra were obtained with Fourier-transform infrared (FTIR) Cary 630 (Agilent Technologies, Santa Clara, Calif., US) with diamond attenuated total reflectance (ATR) spectrophotometer. Nuclear magnetic resonance (NMR)$^1$H and $^{13}$C spectra were recorded using Varian Gemini 200, Varian Unity 300/500 MHz, or Varian Mercury 300/400 systems at room temperature. (Varian Medical Systems, Palo Alto, Calif., US).

Chemical shifts are given in ppm ($\delta$) downfield from tetramethylsilane (TMS). Coupling constants (J) are in Hertz [Hz] and signals are described as follows: s, singlet; d, doublet; t, triplet; q, quadruplet; m, multiplet; br, broad; app, apparent. Analysis of the NMR free induction decays (FIDs) were performed using Mestrenova 6.0.2 software (Mestrelab Research, Santiago de Compostela, Spain). Low resolution mass spectra were obtained on Agilent Technologies 6120 Quadrupole Liquid Chromatography-Mass Spectrometry (LC-MS) in electrospray ionization (ESI) with an Agilent Technologies 1260 Infinity LC system using SeQuant Zic-Hilic (Merck-Millipore) 150 mm×4.6 mm, 5 am column (Agilent Technologies, Santa Clara, Calif., US). Agilent formula predictor software was used to process the data. MS was reported in units of mass to charge ratio (m/z). The analysis was performed with a flow rate of 1 mL/min maintaining the column temperature at 25° C. The detector was set at 214-254 nm±16 nm. Mass Detection: Scan 50-1000 m/z. The mobile phase consisted of phase A (200 mM ammonium acetate, pH 5.2, without ethylenediaminetetraacetic acid (EDTA)) and phase B (acetonitrile 80% and solution of ammonium acetate 20%), isocratic method. High-resolution mass spectrometry analysis (time-of-flight, TOF) was performed using an Agilent 6210 time-of-flight LC/MS. (Agilent Technologies, Santa Clara, Calif., US).

All chemicals were obtained from commercial sources, and used as received without extra purification. Palladium on carbon 10 wt % loading matrix activated carbon support (Pd (C), 205699), ammonia solution 32% (105426) were purchased from Sigma-Aldrich, St. Louis, Mo., US. Thin layer chromatography (TLC) analyses were performed using silica gel (Kieselgel 60 7254, Macherey-Nagel, Duren, Germany) and the spots were visualized under ultraviolet (UV) light. The column chromatography was performed with silica gel 60 (40-63 µm, Merck & Co., Kenilworth, N.J., US) columns, using the eluent reported in each case.

Synthesis of ANTARTINA® was previously described in U.S. Pat. No. 10,058,582 (the entire contents of which are incorporated herein by reference, especially those sections outlining the synthesis of ANTARTINA®).

Adenovirus IL-12 constructs are as previously reported. (Mazzolini et al., *Cancer Gene Therapy*, 6(6):514-522, 1999).

ANTARTINA® was detected and obtained by isolation using semi-preparative high performance liquid chromatography (HPLC) from aqueous extracts of *Deschampsia antarctica* Desv. (Poaceae). The purity and structural identification of the isolated peak 10 was performed by Nuclear Magnetic Resonance (NMR) and analyzed by mass spectrometry (MS). Peak 10 isolated from *Deschampia antarctica* extract, is tricin 7-O-P-D-glucopyranoside, also called 5-hydroxy-2-(4-hydroxy-3,5-dimethoxy-phenyl)-7-[(2S, 3S, 4R, 5S, 6R)-3,4,5-trihydroxy-6-(hydroxymethyl) tetrahydropyran-2-yl] oxychromen-4-one.

Mouse CT26 tumor cell line, an undifferentiated murine colorectal carcinoma (CRC) cell line established from N-nitroso-N-methylurethan-induced transplantable tumor in BALB/c (H-2d) mice, BNL cells (an hepatoma cell line) were used in the studies below and can be obtained from the University of Navarra, Spain. Human cell lines were from American Type Culture Collection (ATCC, Manassas, Va., US), including LoVo (ATCC-CCL229), ASG (ATCC-CCRL-79) and lung fibroblast Wi38 (ATCC-CCL75). All lines were tested for mycoplasma and cultured in complete DMEM (GIBCO, Themo Fisher Scientific, mM glutamine, 100 U/mL penicillin, 100 mg/mL streptomycin, and 10% heat inactivated fetal bovine serum (FBS, GIBCO, Thermo Fisher Scientific) and incubated 37° C. in 5% $CO_2$.

All animals were from Envigo (Barcelona, Spain) and were maintained at the Spanish National Cancer Research Center (CNIO) Animal Facility (AAALAC accredited) in accordance with guidelines stated in the International Guiding Principles for Biomedical Research Involving Animals (CIOMS). All animal experiments were approved by the Competent Authority of Communidad de Madrid (project PROEX 104/16).

Example 1: Synthesis of ANTARTINA® Derivative Tricin 7-O-β-D-glucopyranoside, Per Acetylated (AST-1603-59S2, 6a, FIG. 1)

Scheme 1

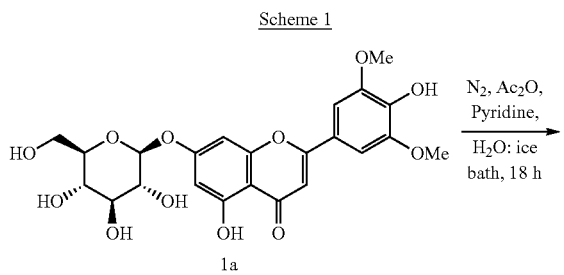

A mixture of Tricin 7-O-β-D-glucopyranoside 1a (0.5 g, 1.02 mmol, 1.0 eq.) and pyridine (14 mL, 173.4 mmol) in a water: ice bath (4° C.) was treated with $Ac_2O$ (14 mL) dropwise. The reaction mixture is warmed up at room temperature and stirred overnight. After that, the solvents were removed under reduced pressure and the residue was treated with methyl-t-butyl ether (MTBE) (50 mL) to obtain 0.5 g (56%) of 6a as a white solid. M. p.: 239.1-241.8° C. 1H-NMR (CDCl3, 500 MHz) δ (ppm): 2.05 (m, 6H), 2.06 (s, 3H), 2.08 (s, 3H), 2.37 (s, 3H), 2.44 (s, 3H), 3.91 (s, 6H), 3.99 (br s, 1H), 4.20 (d, J=11.8 Hz, 1H), 4.28 (dd, J=12.6 Hz, J=5.6 Hz, 1H), 5.17 (t, J=9.0 Hz, 1H), 5.36-5.23 (m, 3H), 6.56 (s, 1H), 6.70 (s, 1H), 7.02 (s, 1H), 7.05 (s, 2H). 13C-RMN (CDCl3, 125 MHz) δ (ppm): 178.8, 173.9, 172.7, 172.3, 172.0, 171.9, 170.9, 164.4, 162.5, 160.8, 155.3, 153.3, 134.2, 131.9, 115.4, 111.6, 111.4, 105.7, 105.6, 100.5, 75.1, 74.8, 73.5, 70.7, 64.6, 59.0, 23.7, 23.2, 23.0. HPLC-UV-MS: tR=15.96 min, Purity (at 254 nm): 98%; MS (ESI, positive mode): m/z=745.2, [M+H]+; MS (ESI, negative mode): m/z=743.1 (M–H)–. HRMS calculated for $C_{35}H_{36}O_{18}$, 744.1902 [M+H]+, found, 744.1902.

Example 2: Synthesis of ANTARTINA® Derivative [3,4,5-triacetoxy-6-[5-hydroxy-2-(4-hydroxy-3,5-dimethoxy-phenyl)-4-oxo-chromen-7-yl]oxy-tetrahydropyran-2-yl]methyl Acetate (AST-1603-097, 5b, FIG. 1)

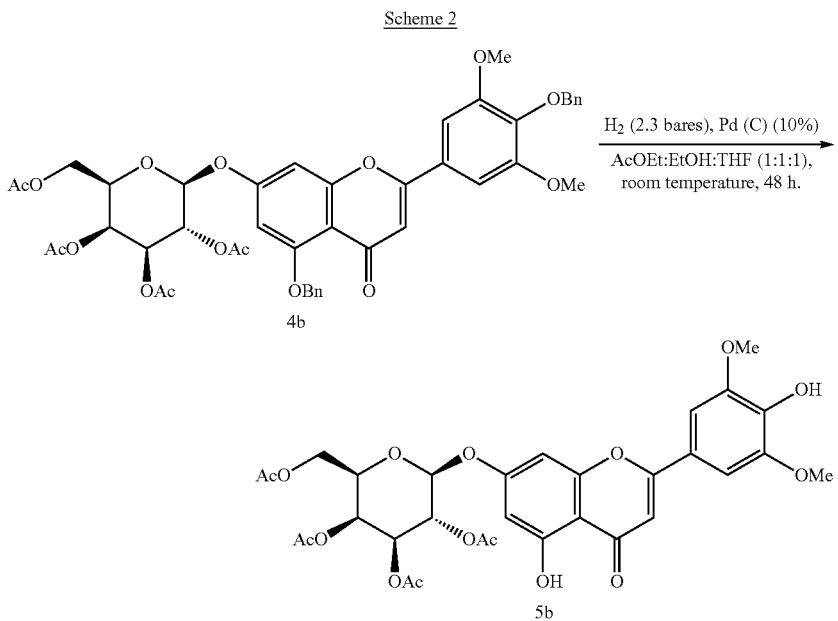

A solution of 4b (6.0 g; 7.14 mmol, 1.0 eq.) in AcOEt: EtOH:THF (1:1:1, 250 mL, 1 g/42 mL) was treated with Pd (C) (10%) (10% w/w, 0.6 g). The reaction mixture was purged with $N_2$ (3×2 bars) and $H_2$ (3×2 bars). Finally, the reaction was treated with $H_2$ (2.3 bars) at room temperature for 48 hours. After that, the reaction mixture was filtered through celite and the solvents were removed under reduced pressure. The residue was treated with $Et_2O$ (50 mL) to obtain 3.50 g (75%) of 3 as a brown-red solid. M. p.: 117.2-121.8° C. 1H-NMR (DMSO-d6, 500 MHz) δ (ppm): 1.95 (s, 3H), 2.01 (s, 3H), 2.05 (s, 3H), 2.15 (s, 3H), 3.88 (s, 6H), 4.12 (br s, 2H), 4.54 (br s, 1H), 5.24 (m, 2H), 5.35 (br s, 1H), 5.68 (br s, 1H), 6.47 (s, 1H), 6.85 (s, 1H), 7.39 (s, 1H), 7.36 (s, 2H), 9.39 (br s, 1H), 13.04 (br s, 1H); 13C-RMN (DMSO-d6, 125 MHz) δ (ppm): 185.2, 173.0, 172.9, 172.6, 172.3, 167.5, 164.7, 164.5, 159.9, 154.9, 151.3 (2C), 143.3, 142.2, 131.0, 127.9, 123.2, 108.9, 107.7 (2C), 106.9, 101.9, 99.9, 98.6, 73.8, 73.3, 71.1, 70.3, 64.6, 59.6, 33.5. HPLC-UV-MS: tR=15.67 min, Purity (at 254 nm): 98%; MS (ESI, positive mode): m/z=661, [M+H]+; MS (ESI, negative mode): m/z=659.0 (M–H)–. HRMS calculated for $C_{31}H_{33}O_{16}$, 661.1763 [M+H]+, found, 661.1731.

-continued

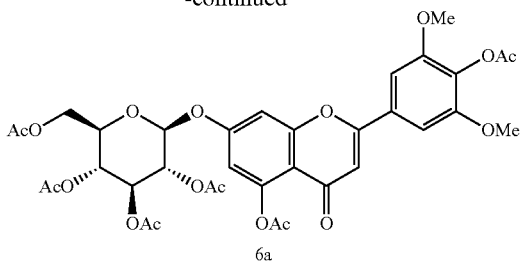

Example 3: Synthesis of ANTARTINA® Derivative 5-hydroxy-2-(4-hydroxy-3,5-dimethoxy-phenyl)-7-[3,4,5-trihydroxy-6-(hydroxymethyl)tetrahydropyran-2-yl]oxy-chromen-4-one (AST-1603-102 SP, 1b, FIG. 1)

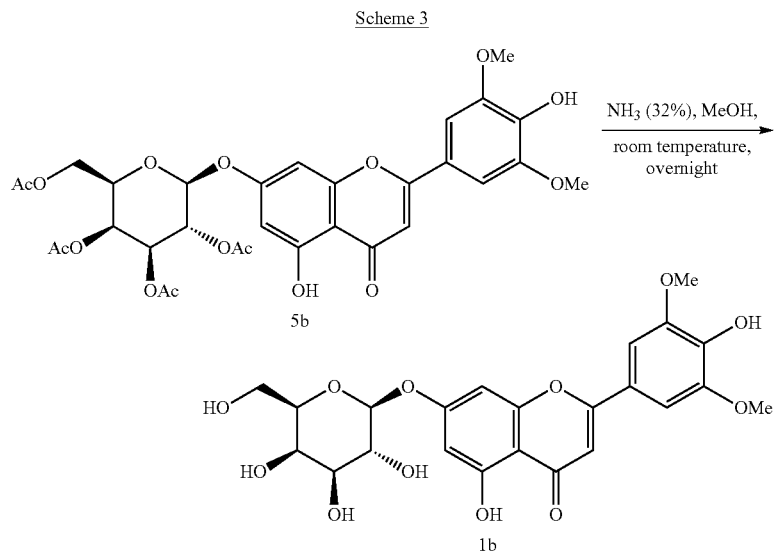

[3,4,5-triacetoxy-6-[5-hydroxy-2-(4-hydroxy-3,5-dimethoxy-phenyl)-4-oxo-chromen-7-yl]oxy-tetrahydropyran-2-yl]methyl acetate (AST-1603-097, 5b, 2.0 g, 3.03 mmol, 1.0 eq.) was dissolved in MeOH (140 mL; 1 g/70 mL) and finally treated with 32% aqueous $NH_3$ solution (62 mL). The reaction mixture was stirred at room temperature overnight. After that, the solvents were removed under reduced pressure. The residue was treated with DMSO (1 mL) and distilled $H_2O$ (10 mL). The solid was removed after filtration isolating 1.0 g (67%) of 1b as a brown solid. M. p.: 260.2-263.3° C. 1H-NMR (DMSO-d6, 500 MHz) δ (ppm): 3.50-3.62 (m, 4H), 3.69 (dt, J=14.0 Hz, J=7.9 Hz, 2H), 3.87 (s, 6H), 4.54 (d, J=4.6 Hz, 1H), 4.71 (t, J=5.5 Hz, 1H), 4.89 (d, J=5.8 Hz, 1H), 4.99 (d, J=7.7 Hz, 1H), 5.22 (d, J=5.2 Hz, 1H), 6.45 (d, J=2.2 Hz, 1H), 6.92 (d, J=2.2 Hz, 1H), 7.06 (s, 1H), 7.35 (s, 2H), 9.36 (br s, 1H), 12.9 (br s, 1H). 13C-RMN (DMSO-d6, 125 MHz) δ (ppm): 185.3, 167.3, 166.3, 163.9, 159.9, 151.3 (2C), 142.9, 123.2, 108.5, 107.4 (2C), 106.9, 104.1, 102.6, 98.1, 78.9, 76.3, 73.2, 71.3, 63.6, 59.5 (2C). HPLC-UV-MS: tR=10.09 min; Purity (at 254 nm): 98.5%; MS (ESI, positive mode): m/z=493, [M+H]+; MS (ESI, negative mode): m/z=491 (M−H)−. HRMS calculated for $C_{23}H_{25}O_{12}$, 493.1340 [M+H]+.

Example 4: Synthesis of ANTARTINA® Xylose Derivative 1c (AST-1608-28, 1c, FIG. 1)

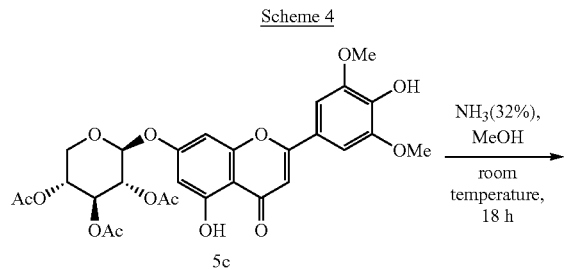

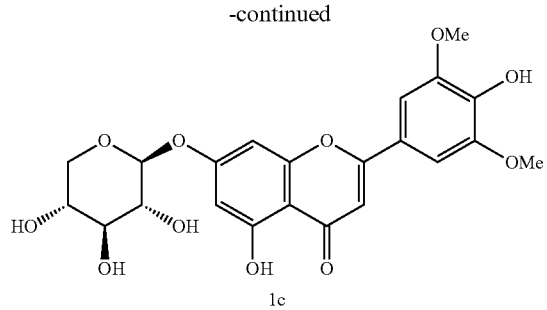

The xylose derivative precursor, (AST1608-13S3) 5c, (2.9 g, 4.9 mmol, 1.0 eq.) was dissolved with MeOH (200 mL, 1 g/70 mL) and treated with 32% aqueous $NH_3$ solution (100 mL). The reaction mixture was stirred at room temperature overnight. After that, the solvents were removed under reduced pressure. The residue was treated with DMSO (2 mL) and distilled $H_2O$ (40 mL). After precipitation, the solid was collected after filtration yielding 1.5 g (66%) of 1c as a pale yellow-brown solid. M. p.: 245.3-249.8° C. 1H-NMR (DMSO-d6, 500 MHz) δ (ppm): 3.19-3.46 (m, 5H), 3.76 (d, J=5.8 Hz, 1H), 3.88 (s, 6H), 5.08 (m, 2H), 5.42 (br s, 1H), 6.42 (d, J=1.6 Hz, 1H), 6.88 (d, J=1.6 Hz, 1H), 7.05 (s, 1H), 7.36 (s, 2H), 9.26 (br s, 2H), 12.90 (br s, 1H). 13C-RMN (DMSO-d6, 125 MHz) δ (ppm): 185.2, 167.3, 165.7, 164.2, 160.0, 151.2 (2C), 143.2, 123.2, 108.5, 107.7 (2C), 106.8, 103.4, 102.5, 98.1, 79.3, 75.9, 72.3, 68.9, 59.5 (2C). HPLC-UV-MS: tR=11.9 min; Purity (at 254 nm): 98.1%; MS (ESI, positive mode): m/z=463.0 [M+H]+, 485 [M+Na]+; MS (ESI, negative mode): m/z=461.0 (M−H)−. HRMS calculated for $C_{22}H_{23}O_{11}$, 463.1234 [M+H]+, found, 463.1208.

Example 5: Synthesis of ANTARTINA® Derivative 7-[(3R,4R,5S,6R)-3,4-dihydroxy-6-(hydroxymethyl)-5-[(3R,4S,5R,6R)-3,4,5-trihydroxy-6-(hydroxymethyl)tetrahydropyran-2-yl]oxy-tetrahydropyran-2-yl]oxy-5-hydroxy-2-(4-hydroxy-3,5-dimethoxy-phenyl)chromen-4-one (AST-1608-77s, 1d, FIG. 1)

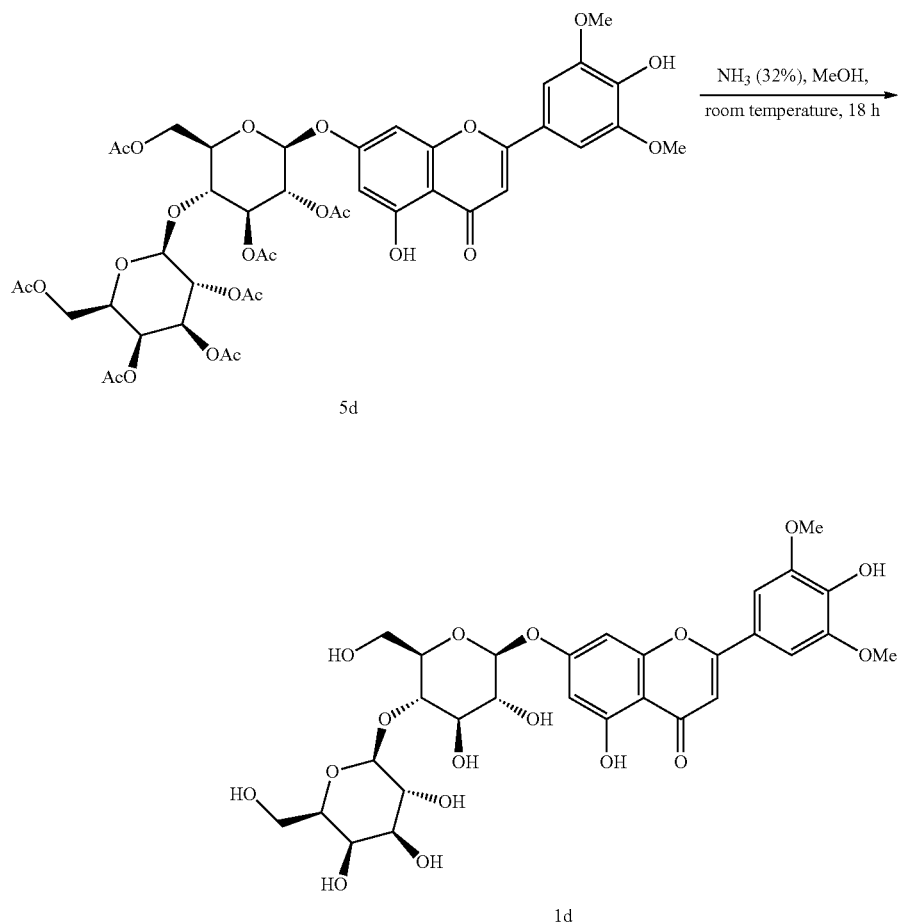

[(2R,3S,4R,5R)-5-acetonyl-4-acetoxy-6-[5-hydroxy-2-(4-hydroxy-3,5-dimethoxy-phenyl)-4-oxo-chromen-7-yl]oxy-3-[(3R,4S,5S,6R)-3,4,5-triacetoxy-6-(acetoxy methyl) tetrahydropyran-2-yl]oxy-tetrahydropyran-2-yl]methyl acetate (AST-1608-69) 5d (4.0 g, 4.22 mmol, 1.0 eq.) was dissolved with MeOH (280 mL, 1 g/70 mL) and finally treated with 32% aqueous NH$_3$ solution (104 mL). The reaction mixture was stirred overnight at room temperature. After that, the solvents were removed under reduced pressure. The residue was treated with DMSO (2 mL) and distilled H$_2$O (20 mL). The solid was removed after filtration isolating 1.6 g (58%) of 1d as a pale yellow-brown solid. M. p.: 275.4-279.2° C. 1H-NMR (DMSO-d6, 500 MHz) δ (ppm): 3.38 (dd, J=15.7 Hz, J=6.4 Hz, 2H), 3.44-3.57 (m, 5H), 3.63 (m, 4H), 3.80 (dd, J=10.3 Hz, J=5.2 Hz, 1H), 3.88 (s, 6H), 4.23 (d, J=7.2 Hz, 1H), 4.52 (d, J=4.6 Hz, 1H) 4.67 (dd, J=12.6 Hz, J=5.7 Hz, 2H), 4.78 (d, J=5.1 Hz, 1H), 4.83 (d, J=1.3 Hz, 1H), 5.08 (d, J=4.5 Hz, 1H), 5.15 (d, J=7.8 Hz, 1H), 5.55 (d, J=5.3 Hz, 1H), 6.47 (d, J=2.0 Hz, 1H), 6.93 (d, J=2.0 Hz, 1H), 7.07 (s, 1H), 7.35 (s, 1H), 9.36 (br s, 2H), 12.9 (br s, 1H). 13C-RMN (DMSO-d6, 125 MHz) δ (ppm): 185.0, 167.2, 165.9, 164.1, 159.9, 151.3 (2C), 143.1, 123.2, 108.5, 107.6 (2C), 106.7, 102.5, 98.3, 83.1, 78.7, 78.3, 77.8, 76.4, 75.9, 73.7, 71.3, 63.5, 63.0, 59.6 (2C). HPLC-UV-MS: tR=10.06 min; Purity (at 254 nm): 95.4%; MS (ESI, positive mode): m/z=655 [M+H]+; MS (ESI, negative mode): m/z=653.3 (M−H)−. HRMS calculated for C$_{29}$H$_{35}$O$_{17}$, 665.1868 [M+H]+, found, 655.1835.

Example 6: Synthesis of ANTARTINA® Derivative 7-[(3R,4R,5S,6R)-3,4-dihydroxy-6-(hydroxymethyl)-5-[(3R,4S,5S,6R)-3,4,5-trihydroxy-6-(hydroxymethyl)tetrahydropyran-2-yl]oxy-tetrahydropyran-2-yl]oxy-5-hydroxy-2-(4-hydroxy-3,5-dimethoxy-phenyl)chromen-4-one (AST-1608-21, 1e, FIG. 1)

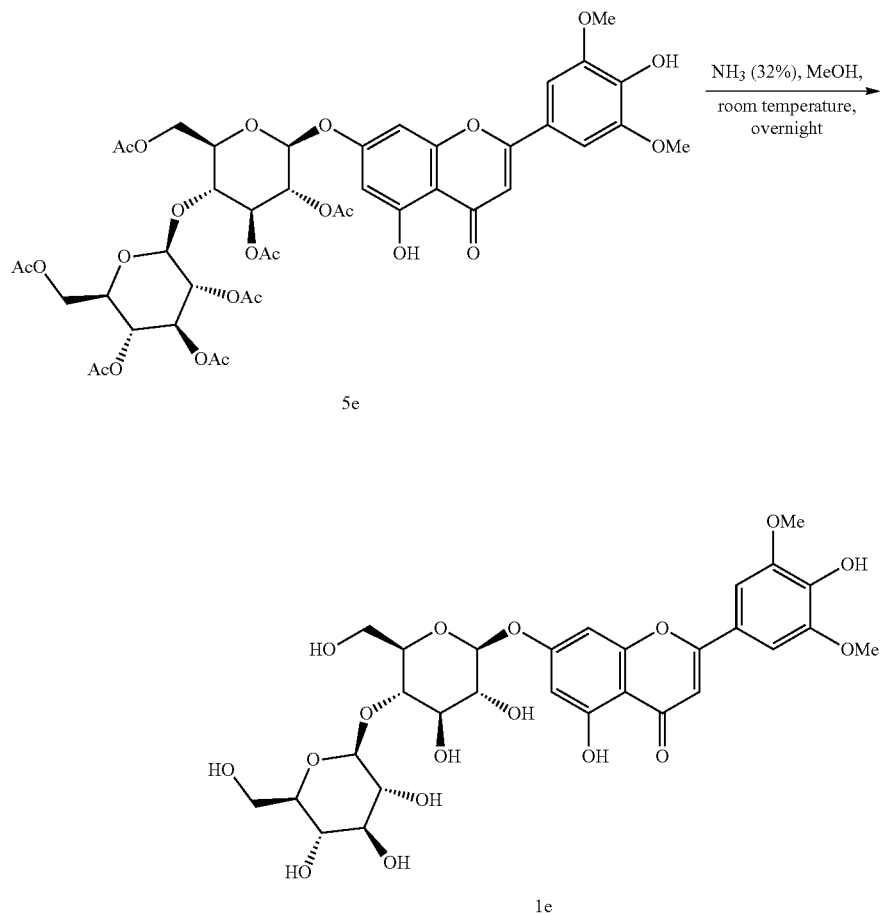

[(2R,3S,4R,5R)-5-acetonyl-4-acetoxy-6-[5-hydroxy-2-(4-hydroxy-3,5-dimethoxy-phenyl)-4-oxo-chromen-7-yl]oxy-3-[(3R,4S,5R,6R)-3,4,5-triacetoxy-6-(acetoxy methyl)tetrahydropyran-2-yl]oxy-tetrahydropyran-2-yl]methyl acetate (AST-1608-16) 5e (3.89 g, 4.1 mmol, 1.0 eq.) was dissolved with MeOH (280 mL, 1 g/72 mL) and finally treated with 32% aqueous $NH_3$ solution (104 mL). The reaction mixture was stirred at room temperature overnight. After that, the solvents were removed under reduced pressure. The residue was treated with DMSO (3 mL) and distilled $H_2O$ (30 mL). The solid was collected after filtration, isolating 1.7 g (64%) of 1e as a pale yellow-brown solid. M. p.: 243.2-246.5° C. 1H-NMR (DMSO-d6, 500 MHz) δ (ppm): 2.96-3.10 (m, 2H), 3.19 (m, 3H), 3.40 (dd, J=19.9 Hz, J=11.9 Hz, 2H), 3.47 (dt, J=12.0 Hz, J=9.5 Hz, 1H), 3.64 (m, 2H), 3.67-3.74 (m, 2H), 3.79 (dd, J=10.2 Hz, J=4.7 Hz, 1H), 3.87 (s, 6H), 4.28 (d, J=7.9 Hz, 1H), 4.60 (t, J=5.2 Hz, 1H), 4.69 (t, J=5.6 Hz, 1H), 4.82 (d, J=1.9 Hz, 1H), 5.06-4.94 (m, 2H), 5.14 (d, J=7.8 Hz, 1H), 5.22 (d, J=4.7 Hz, 1H), 5.54 (d, J=5.1 Hz, 1H), 6.46 (d, J=2.1 Hz, 1H), 6.92 (d, J=2.1 Hz, 1H), 6.46 (d, J=2.1 Hz, 1H), 6.92 (d, J=2.1 Hz, 1H), 7.06 (s, 1H), 7.35 (s, 1H), 9.33 (br s, 2H), 12.9 (br s, 1H). 13C-RMN (DMSO-d6, 125 MHz) δ (ppm): 185.1, 167.2, 165.9, 164.2, 159.9, 151.3 (2C), 143.1, 123.0, 108.5, 107.6 (2C), 106.9, 106.2, 102.7, 102.5, 98.3, 82.9, 79.8, 79.5, 78.4, 77.9, 76.4, 75.9, 73.1, 64.2, 63.0, 59.4 (2C). HPLC-UV-MS: tR=10.20 min; Purity (at 254 nm): 100%; MS (ESI, positive mode): m/z=655 [M+H]+, 677 [M+Na]+; MS (ESI, negative mode): m/z=653.3 (M−H)−. HRMS calculated for $C_{29}H_{35}O_{17}$, 665.1868 [M+H]+, found, 665.1833.

Example 7: Synthesis of ANTARTINA® Derivative 7-[(2S,3R,4R,5S,6R)-3,4-dihydroxy-6-(hydroxymethyl)-5-[(2S,3R,4S,5S,6R)-3,4,5-trihydroxy-6-(hydroxymethyl)tetrahydropyran-2-yl]oxy-tetrahydropyran-2-yl]oxy-5-hydroxy-2-(4-hydroxy-3,5-dimethoxy-phenyl)chromen-4-one (AST-1608-73s, 1f, FIG. 1)

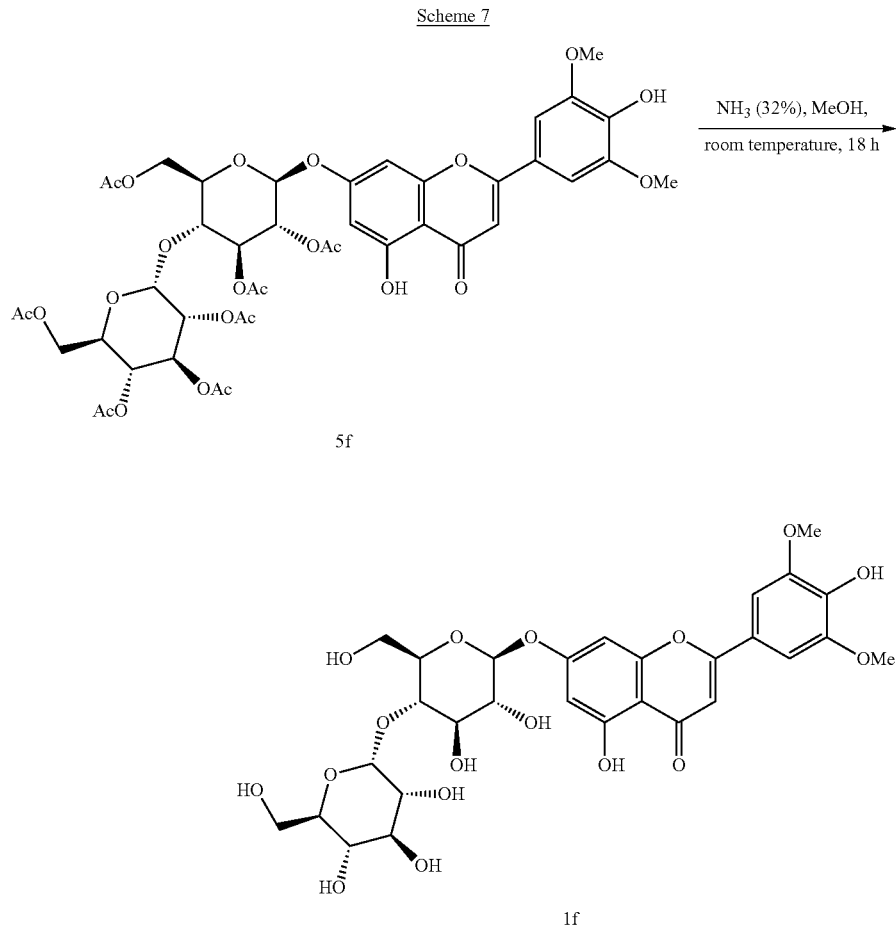

[(2R,3S,4R,5R,6S)-5-acetonyl-4-acetoxy-6-[5-hydroxy-2-(4-hydroxy-3,5-dimethoxy-phenyl)-4-oxo-chromen-7-yl]oxy-3-[(3R,4S,5R,6R)-3,4,5-triacetoxy-6-(acetoxymethyl)tetrahydropyran-2-yl]oxy-tetrahydropyran-2-yl]methyl acetate (AST1608-67) 5f (2.89 g, 2.95 mmol, 1.0 eq.) was dissolved with MeOH (202 mL, 1 g/70 mL) and finally treated with 32% aqueous $NH_3$ solution (75 mL). The reaction mixture was stirred at room temperature overnight. After that, the solvents were removed under reduced pressure. The residue was treated with DMSO (2 mL) and distilled $H_2O$ (20 mL). The solid was collected after filtration yielding 1.6 g (58%) of 1f as a pale yellow-brown solid. M. p.: 114.7-194.4° C. 1H-NMR (DMSO-d6, 500 MHz) δ (ppm): 3.06 (t, J=8.1 Hz, 2H), 3.20-3.52 (m, 5H), 3.54-3.65 (m, 5H), 3.74 (d, J=10.9 Hz, 1H), 3.86 (s, 6H), 4.63 (br s, 3H), 4.91 (br s, 2H), 5.05 (d, J=3.6 Hz, 1H), 5.11 (d, J=7.7 Hz, 1H), 5.55 (br s, 4H), 6.44 (d, J=1.9 Hz, 1H), 6.90 (d, J=1.9 Hz, 1H), 7.03 (s, 1H), 7.31 (s, 2H). 13C-RMN (DMSO-d6, 125 MHz) δ (ppm): 185.1, 167.2, 166.0, 164.2, 159.9, 151.3 (2C), 143.3, 123.2, 108.5, 107.6 (2C), 106.8, 103.8, 102.8, 102.6, 98.3, 82.0, 79.2, 78.6, 76.6, 76.4, 75.8, 75.5, 72.9, 63.9, 63.3, 59.4 (2C). HPLC-UV-MS: tR=10.09 min; Purity (at 254 nm): 96.1%; MS (ESI, positive mode): m/z=655 [M+H]+; MS (ESI, negative mode): m/z=653.3 (M−H)−. HRMS calculated for $C_{29}H_{35}O_{17}$, 665.1868 [M+H]+, found, 655.1836.

Example 8: Cell Viability Assays in HEPA129 and CT26 Cells

Figure 2A:
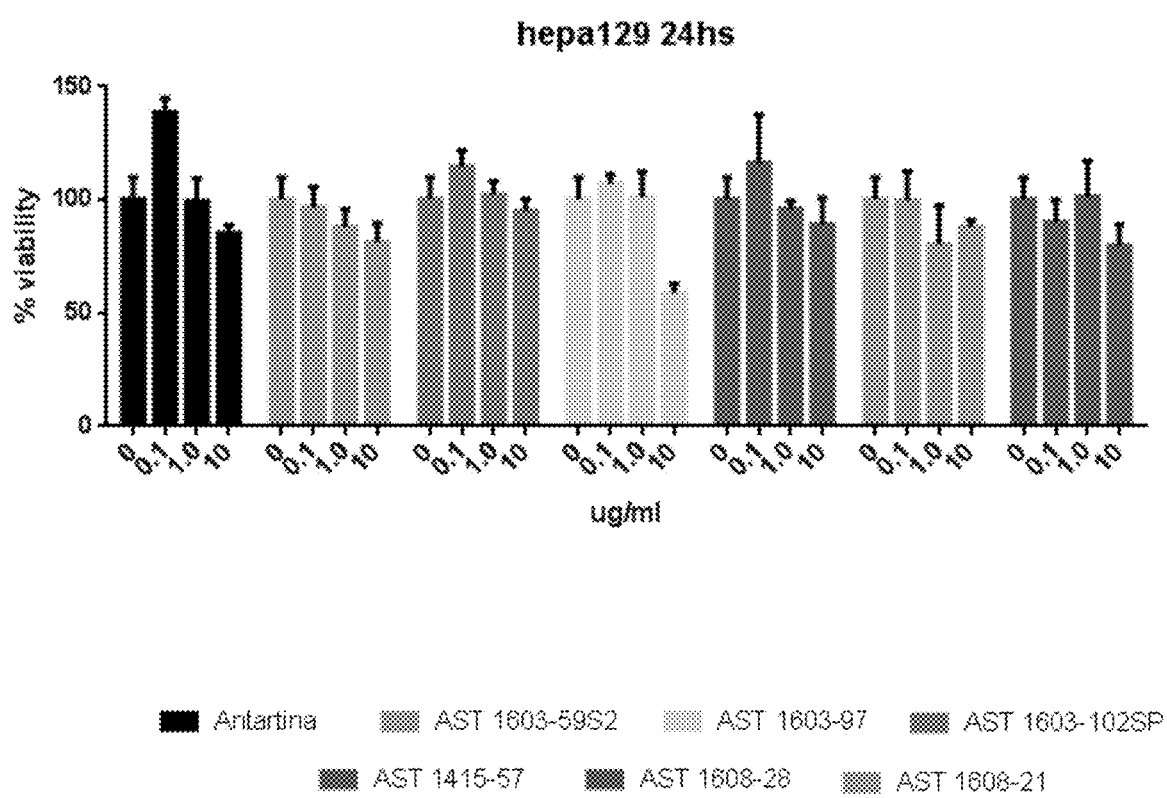
FIGS. 2A, 2B, and 2C depict MTT assay absorbance data obtained from incubation of ANTARTINA® and related derivatives with HEPA129 cells at various time points, including: 24 hrs (FIG. 2A), 48 hrs (FIG. 2B), and 72 hrs (FIG. 2C).
Figure 2B:
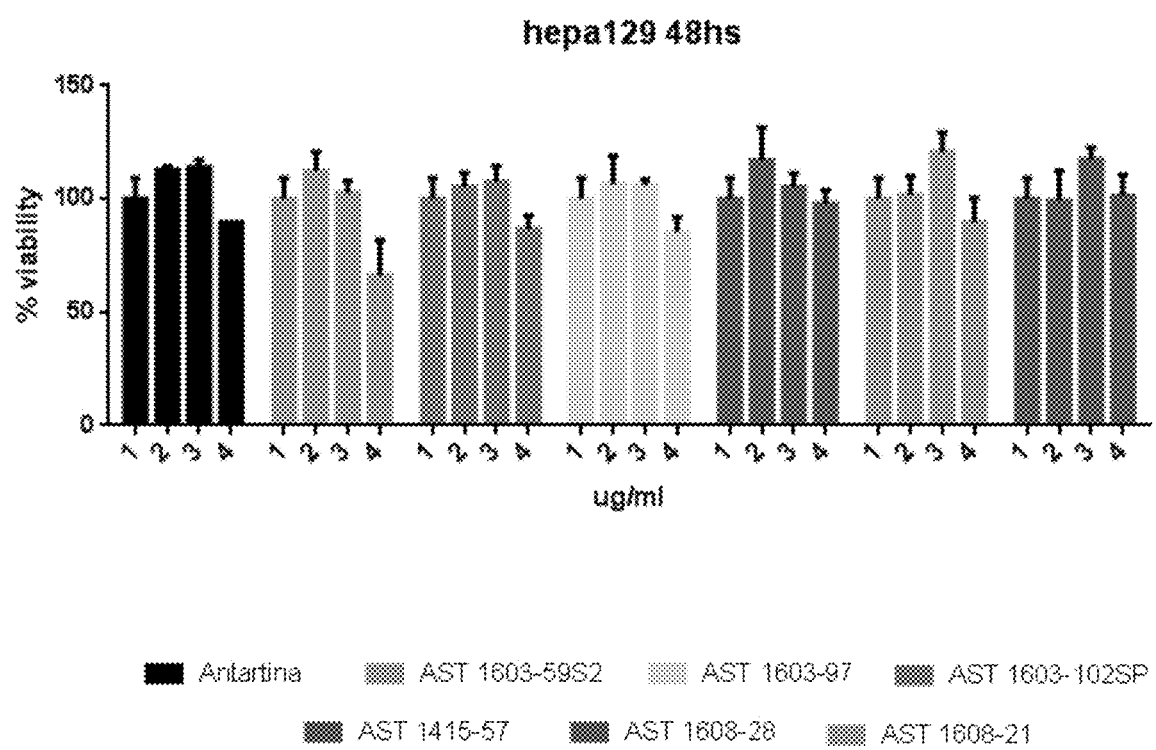
Figure 2C:
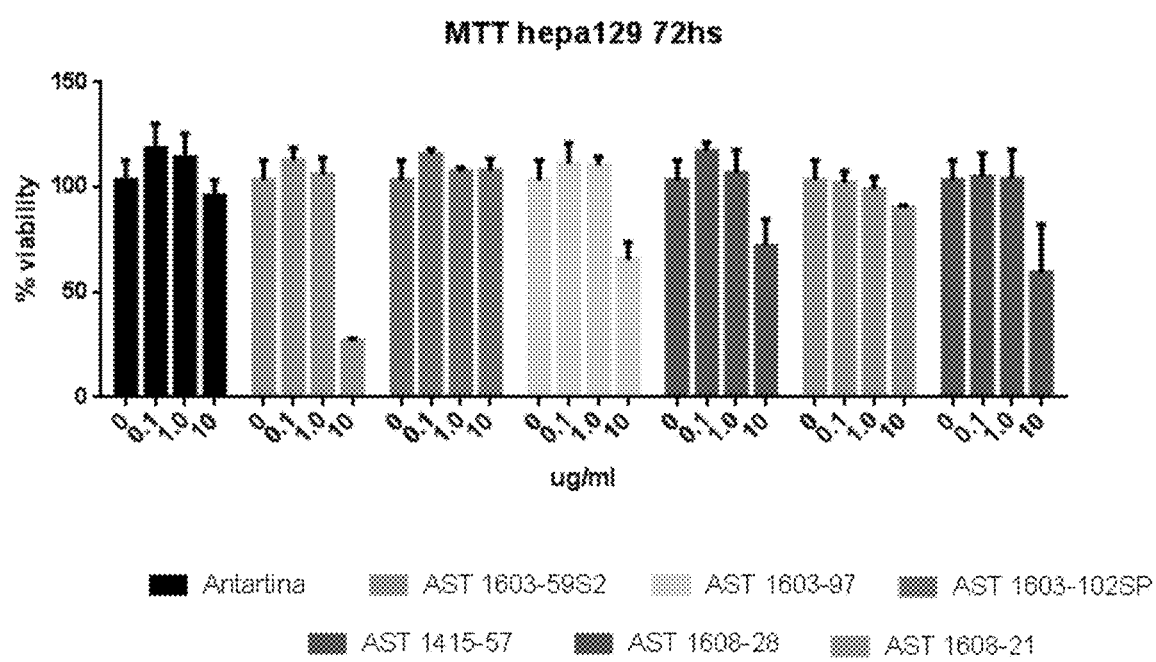

After synthesis of ANTARTINA® and derivatives, the molecules were tested for cytotoxicity in various cancer cell lines. For this, a cell viability test was performed. Briefly, gastric cancer cells, AGS, colon cancer, Lovo (human CRC cell line), and as a control the Wi38 lung fibroblast line were employed. The cells were exposed to decreasing concentrations of molecules 1 and 3 from 1000 μM for 72 hrs. The negative control was just dimethyl sulfoxide (DMSO), the solvent in which the molecules to be tested were dissolved, with no active agent. Afterwards the cells were washed and the MTS (tetrazolium dye) colorimetric compound was added for the MTT assay. It was determined that molecules 1 and 3 were able to inhibit approximately in 50% the cell viability of the AGS and Lovo cancer lines at a concentration of 1000 and 500 μM, as shown in FIG. 2.

Figure 3A:
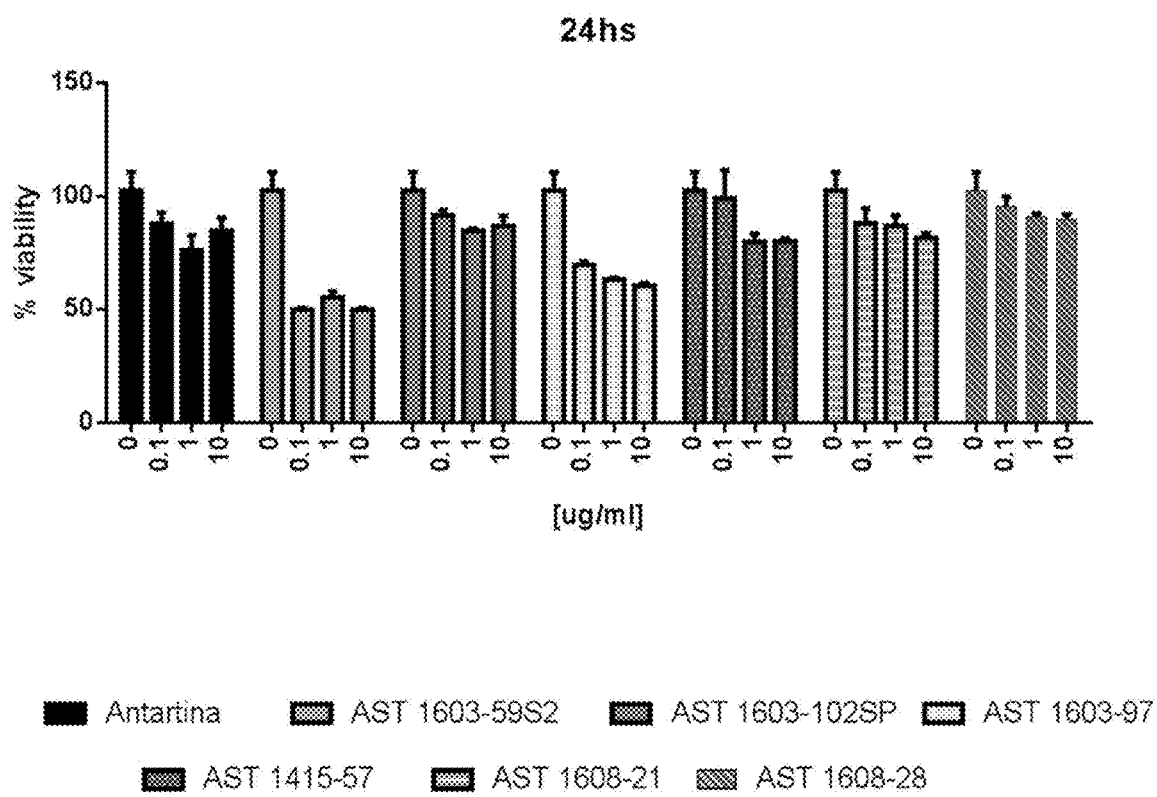
FIGS. 3A, 3B, and 3C depict MTT assay absorbance data obtained from incubation of ANTARTINA® and related derivatives with CT26 cells at various time points, including: 24 hrs (FIG. 3A), 48 hrs (FIG. 3B), and 72 hrs (FIG. 3C).
Figure 3B:
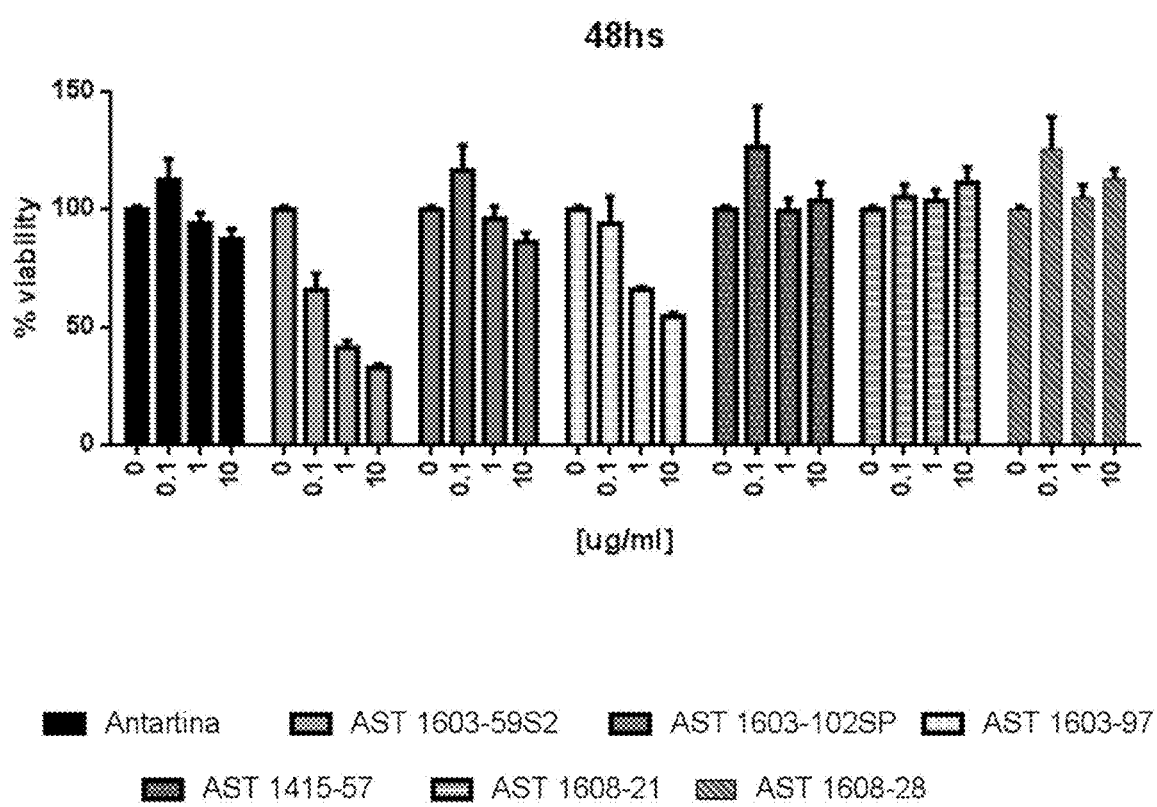
Figure 3C:
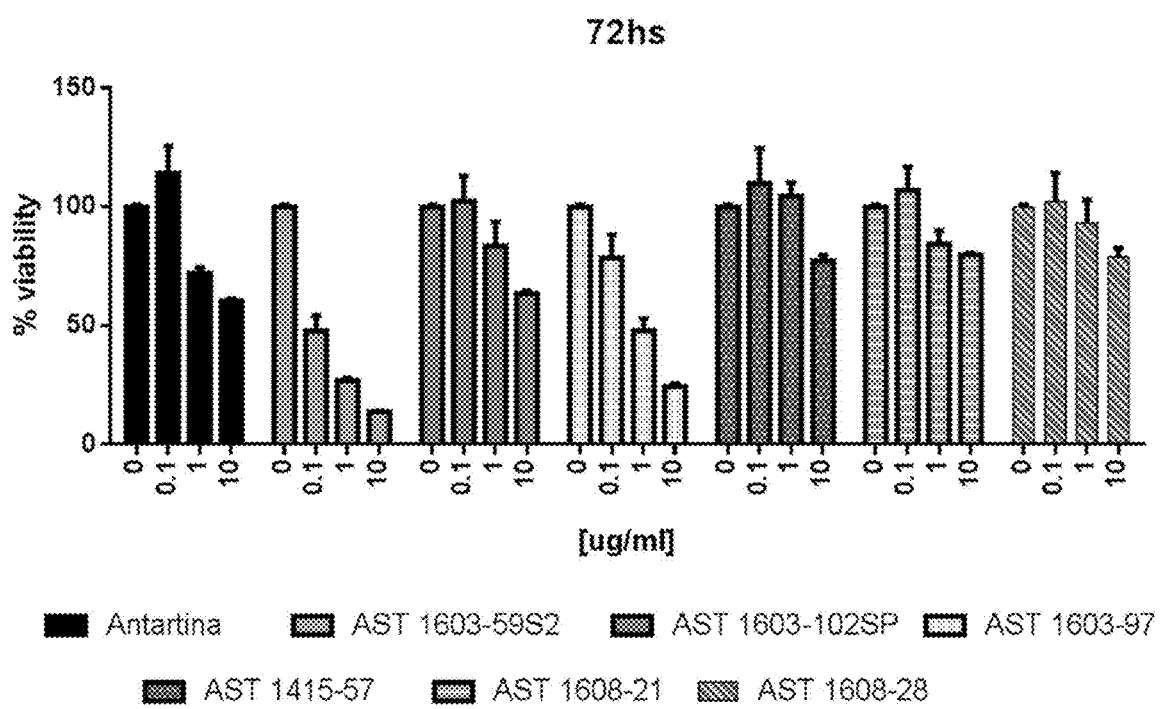

Hepa129 (FIGS. 2A, 2B, and 2C) and CT26 (FIGS. 3A, 3B, and 3C) cells were plated onto 96-well plates at a density of 5×10³ cells/well and cultured with Dulbecco's Modified Eagle Medium (DMEM), 0.1% DMSO, or ANTARTINA® analogues at different doses (0.1, 1.0, 10 μg/ml). Twenty four hours (FIGS. 2A and 3A), 48 hr (FIGS. 2B and 3B) and 72 hrs (FIGS. 2C and 3C) after treatment, viability was determined by the MTT assay (Promega Corp., Madison, Wis., US). The plates were incubated for 4 h and the absorbance of each well was read at 490 nm. All assays were performed in quadruplicate, and each assay was repeated at least twice.

Example 9: Acetylated ANTARTINA® Exerts a Potent Antitumoral Effect in Mice with CRC that is Superior to Native ANTARTINA®

Figure 4:
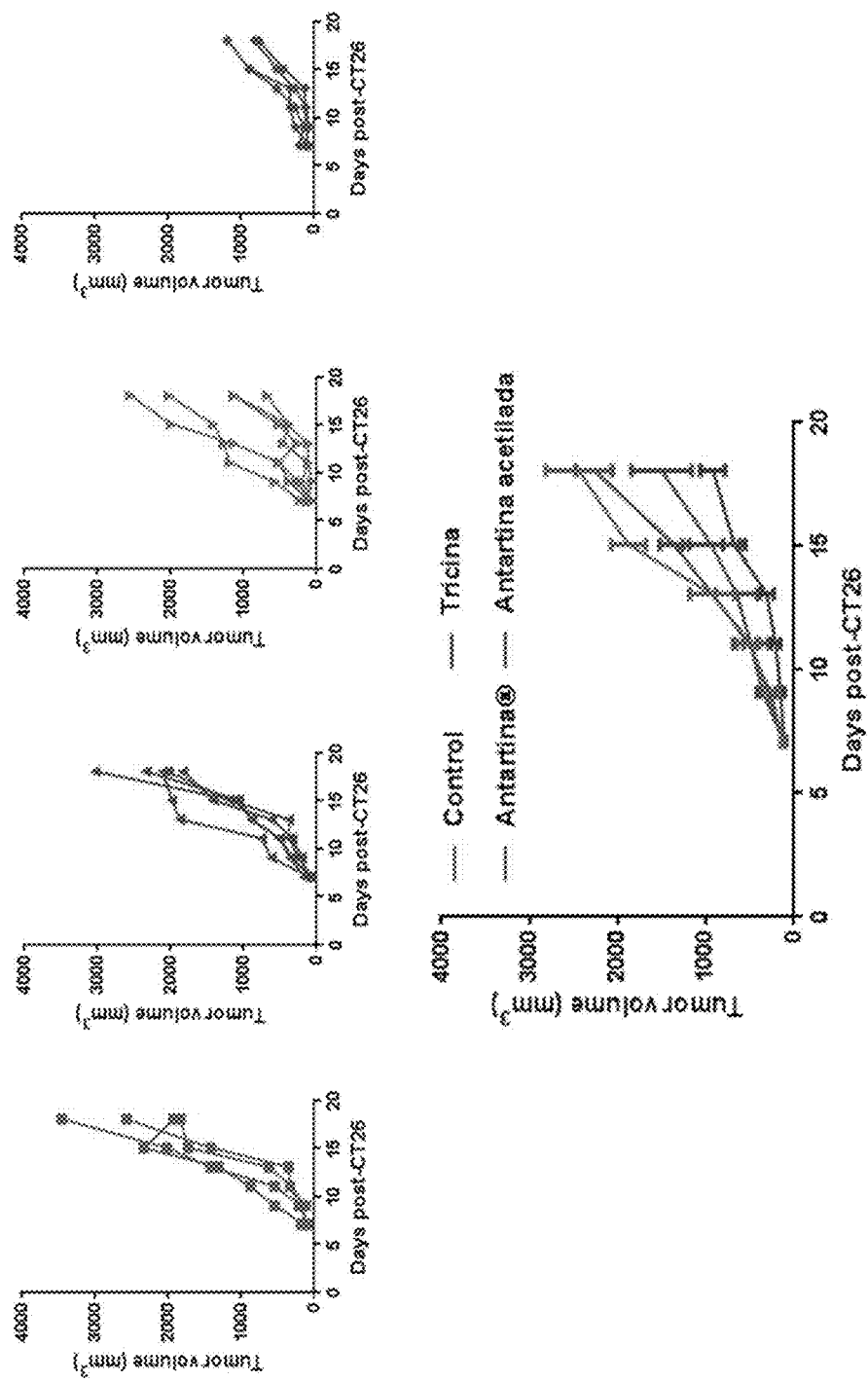
FIG. 4 depicts cell size ($mm^3$) in mice of CT26 tumors after CT26 cell line injection into mice. From left to right, first panel are the results of a control containing only carrier, second panel is treatment of the mouse with tricin, third panel shows the results of treatment of the mouse with ANTARTINA®, and the last panel on the right shows treatment of the mouse with acetylated ANTARTINA®. The bottom panel provides a summary of all results in one graph.

Subcutaneous CRC model: Six-to-eight-week-old male BALB/c mice were used. CT26 cells were injected at a dose of 5×10⁵ cells subcutaneously (s.c.) into the right flank of BALB/c mice (day 0). Tumors were allowed to reach ~90 mm³ in size before treatment. Animals were distributed in different groups and then treated with 0.1% DMSO in sterile water i.p. (control group, n=5), ANTARTINA® (50 mg/kg i.p., day 8, n=5), tricin (50 mg/kg n=8), or acetylated ANTARTINA® (50 mg/kg i.p., day 8, n=5), 3 times per week over the course of 3 weeks. (See, FIG. 3, top graphs, left to right: control, ANTARTINA®, tricin, and acetylated ANTARTINA®). Tumor growth was assessed by caliper measurement. Tumor volume was calculated using the following formula: tumor volume (mm³)=length×(width)²/2. FIG. 4 shows that acetylated ANTARTINA® clearly and markedly reduced tumor size at a higher rate than observed for any of the other tested agents.

Figure 5A:
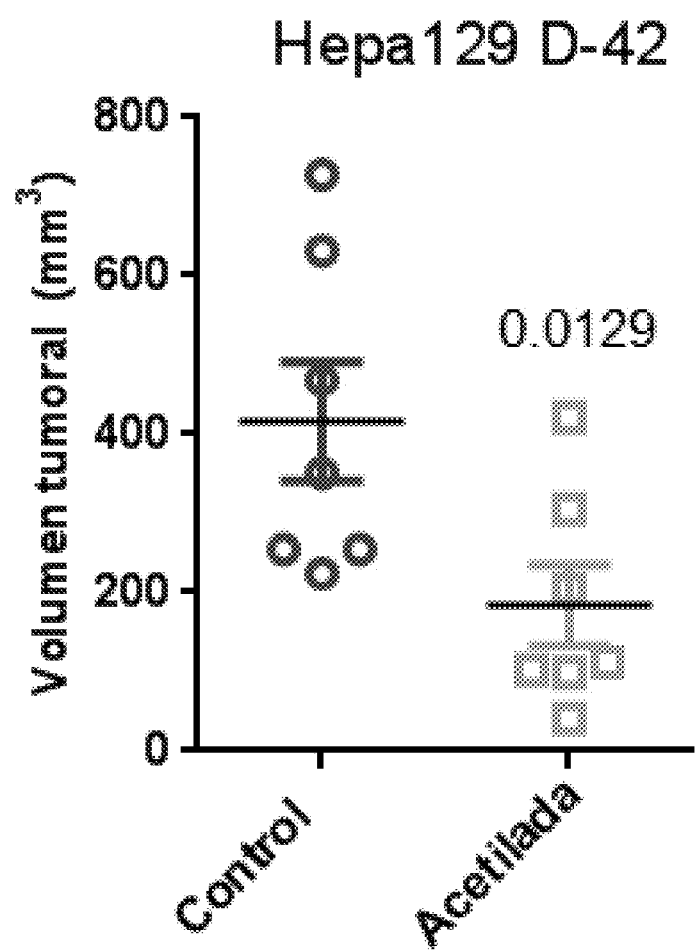
FIG. 5A shows tumor volume vs. treatment for C3H/He mice that were injected with 200 mg/kg of thioacetamide. On day 28, mice were anesthetized and orthotopic tumors were established by sub-capsular inoculation of $1.25 \times 10^5$ Hepa129 cells into the left liver lobe by laparotomy (day 0). Five days after tumor implantation, mice were distributed in groups (n=6-8/group) and received: i) saline (control, FIG. 5A, left panel); ii) acetylated ANTARTINA® (50 mg/kg, 3 times per week, FIG. 5A, right panel). Fifteen days after tumor implantation, mice were sacrificed and tumor volume was quantified, as depicted in FIG. 5B (control, left panel; acetylated ANTARTINA®, right panel).
Figure 5B:
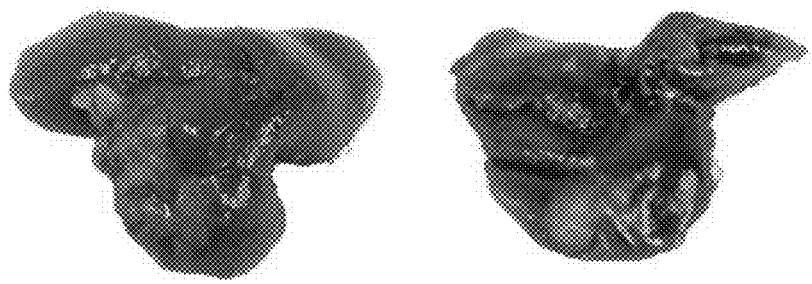

Example 10: Antitumoral Effects of Acetylated ANTARTINA® in an Orthotopic Hepatocellular Carcinoma Model in Mice Experimental model of HCC associated with fibrosis: C3H/He mice were treated intraperitoneally (i.p) with 200 mg/kg of thioacetamide (TAA) (Sigma-Aldrich, St. Louis, USA) 3 times a week for 4 weeks. On day 28, mice were anesthetized and orthotopic tumors were established by sub-capsular inoculation of 1.25×10⁵ Hepa129 cells into the left liver lobe by laparotomy (day 0). Five days after tumor implantation, mice were distributed in groups (n=6-8/group) and received: i) saline (control); ii) acetylated ANTARTINA® (50 mg/kg, 3 times per week). (See, FIG. 5A). Fifteen days after tumor implantation, mice were sacrificed and tumor volume was quantified. (See, FIG. 5B). Acetylated ANTARTINA® markedly reduced the tumor volume.

Example 11: ANTARTINA® in Combination with Immuno-Gene Therapy (Adenovirus-IL12) Shows a Synergistic Antitumoral Effect In preclinical models of cancer, gene therapy with interleukin 12 (IL-12) has reached unprecedented levels of success when combined with immunotherapy approaches such as gene transfer of other cytokines and/or chemokines, costimulatory molecules, or adoptive cell therapy. (Melero et al., *Trends Immunol.*, 22(3):113-115, 2001).

Figure 6:
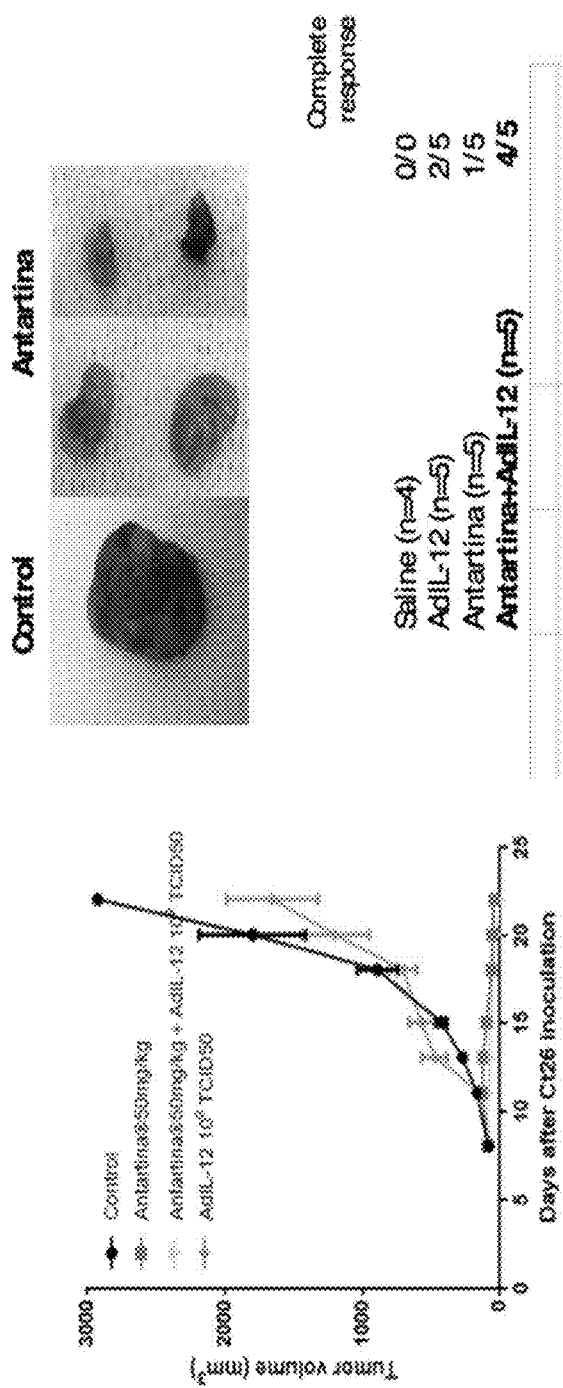
FIG. 6 shows effect of ANTARTINA® and IL-12 gene therapy in combination on a murine model of CRC (CT26 cells) established in BALB/c mice. Mouse CT26 cells ($5 \times 10^5$) were subcutaneously inoculated on day 0. On day 7, when tumors reached a diameter of 5-7 mm, animals were divided into 4 groups: saline, ANTARTINA®, AdIL12, and the combination of ANTARTINA® and AdIL-12. Tumor volume is shown in the left panel vs. days after CT26 inoculation. Excised tumors are depicted in the right panel.

This is a murine model of CRC (CT26 cells) established in BALB/c mice. Mouse CT26 cells (5×10⁵) were subcutaneously inoculated on day 0. On day 7, when tumors reached a diameter of 5-7 mm, animals were divided into 4 groups: saline, ANTARTINA® 50 mg/kg, 3 doses per week (systemically), AdIL12 (adenovirus encoding murine IL-12, dose: 10⁹ TCID50, intratumorally, one dose at day 15 after tumor inoculation), and the combination of ANTARTINA® and AdIL-12. Tumor volume was measured with a caliper 3 times per week. A synergistic antitumor effect was observed for AdIL-12+ANTARTINA®. Complete tumor regressions: saline 0/0, AdIL-12 1/5, Antartina 2/5, and combined therapy: 4/5. (FIG. 6).

The breadth and scope of the present disclosure should not be limited by any of the above-described exemplary embodiments, but should be defined only in accordance with the following claims and their equivalents.

What is claimed is:

1. A method of treating colorectal cancer or hepatocellular carcinoma in a subject in need thereof, which comprises:
    administering a pharmaceutically effective composition comprising one or more derivatives of tricin 7-O-β-D-glucopyranoside,
    wherein the one or more derivatives of tricin 7-O-β-D-glucopyranoside is one or more of:
    hexa-acylated tricin 7-O-β-D-glucopyranoside (6a),
    [3,4,5-triacetoxy-6-[5-hydroxy-2-(4-hydroxy-3,5-dimethoxy-phenyl)-4-oxo-chromen-7-yl]oxy-tetrahydropyran-2-yl]methyl acetate (5b),
    xylose tricin 7-O-β-D-glucopyranoside (1c),
    7-[(3R,4R,5S,6R)-3,4-dihydroxy-6-(hydroxymethyl)-5-[(3R,4S,5R,6R)-3,4,5-trihydroxy-6-(hydroxyrn-ethyl)tetrahydropyran-2-yl]oxy-tetrahydropyran-2-yl]oxy-5-hydroxy-2-(4-hydroxy-3,5-dimethoxy-phenyl)chromen-4-one (1d),
    7-[(3R,4R,5S,6R)-3,4-dihydroxy-6-(hydroxymethyl)-5-[(3R,4S,5S,6R)-3,4,5-trihydroxy-6-(hydroxym-ethyl)tetrahydropyran-2-yl]oxy-tetrahydropyran-2-yl]oxy-5-hydroxy-2-(4-hydroxy-3,5-dimethoxy-phenyl)chromen-4-one (1e), and
    7-[(2S,3R,4R,5S,6R)-3,4-dihydroxy-6-(hydroxym-ethyl)-5-[(2S,3R,4S,5S,6R)-3,4,5-trihydroxy-6-(hy-droxymethyl)tetrahydropyran-2-yl]oxy-tetrahydropyran-2-yl]oxy-5hydroxy-2-(4-hydroxy-3,5-dimethoxy-phenyl)chromen-4-one.

2. The method of claim 1, wherein the subject is human.

3. The method of claim 1, wherein the colorectal cancer is an adenocarcinoma, a gastrointestinal carcinoid tumor, a colorectal lymphoma, or a gastrointestinal stromal tumor.

4. The method of claim 1, wherein one of the one or more derivatives of tricin 7-O-β-D-glucopyranoside is hexa-acylated tricin 7-O-β-D-glucopyranoside.

5. The method of claim 1, wherein the cancer is a hepatocellular carcinoma.

6. The method of claim 5, wherein one of the one or more derivatives of tricin 7-O-β-D-glucopyranoside is hexa-acylated tricin 7-O-β-D-glucopyranoside (6a).

7. The method of claim 1, wherein the method of treating is capable of reducing proliferation of colon cancer cells or hepatocellular carcinoma cells, and/or reducing size of a tumor.

8. The method of claim 1, further comprising administering to the subject one or more additional antitumor agents in a combination anticancer therapy.

9. The method of claim 8, wherein the one or more additional antitumor agents is one or more checkpoint inhibitors.

10. A method of reducing proliferation of colorectal cancer cells or hepatocellular carcinoma cells, and/or reducing size of a tumor, wherein the method comprises administering to the subject in need thereof a pharmaceutically effective amount of hexa-acylated tricin 7-O-β-D-glucopyranoside (6a).

* * * * *